(12) United States Patent
Neil et al.

(10) Patent No.: US 8,658,973 B2
(45) Date of Patent: Feb. 25, 2014

(54) AUGER ELEMENTAL IDENTIFICATION ALGORITHM

(71) Applicants: Mark Neil, San Jose, CA (US); Mehran Nasser-Ghodsi, Hamilton, MA (US); Christopher Sears, Fremont, CA (US)

(72) Inventors: Mark Neil, San Jose, CA (US); Mehran Nasser-Ghodsi, Hamilton, MA (US); Christopher Sears, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/913,240

(22) Filed: Jun. 7, 2013

(65) Prior Publication Data
US 2013/0341504 A1  Dec. 26, 2013

Related U.S. Application Data

(60) Provisional application No. 61/658,494, filed on Jun. 12, 2012.

(51) Int. Cl.
H01J 37/26   (2006.01)

(52) U.S. Cl.
CPC ..................................... H01J 37/26 (2013.01)
USPC ....................................................... 250/305

(58) Field of Classification Search
USPC ....................................................... 250/305
See application file for complete search history.

(56) References Cited

U.S. PATENT DOCUMENTS

| 5,299,138 A | 3/1994 | Fiori et al. |
| 5,754,620 A | 5/1998 | Hossain et al. |

(Continued)

FOREIGN PATENT DOCUMENTS

| GB | 2482680 A | 2/2012 |
| JP | 2002195965 A | 7/2002 |
| JP | 2005292085 A | 10/2005 |
| WO | 0205213 A | 1/2002 |
| WO | 2004061388 A | 7/2004 |

OTHER PUBLICATIONS

Henning Buddenbaum et al. "The Effects of Spectral Pretreatments on Chemometric Analyses of Soil Profiles Using Laboratory Imaging Spectroscopy" Received Feb. 17, 2012; Revised May 11, 2012; Accepted Sep. 18, 2012.

(Continued)

*Primary Examiner* — Kiet T Nguyen
(74) *Attorney, Agent, or Firm* — Joshua D. Isenberg; JDI Patent (57) ABSTRACT

System and methods for decomposing an Auger electron spectrum into elemental and chemical components, includes conditioning and input spectrum to generate a normalized input spectrum; determining statistical correlation between the normalized input spectrum and stored elemental spectral signatures; and characterizing elemental or chemical species in the input spectrum from the statistical correlation, wherein said conditioning the input spectrum includes estimating a background signal of non-Auger electrons in the input spectrum and subtracting the estimated background signal from the input spectrum.

20 Claims, 7 Drawing Sheets

(56) References Cited

U.S. PATENT DOCUMENTS

| | | | |
|---|---|---|---|
| 6,399,944 B1 * | 6/2002 | Vasilyev et al. | 250/310 |
| 6,675,106 B1 | 1/2004 | Keenan et al. | |
| 6,891,158 B2 | 5/2005 | Larson et al. | |
| 7,411,188 B2 | 8/2008 | Dececco et al. | |
| 7,635,842 B2 | 12/2009 | Nasser-Ghodsi et al. | |
| 7,912,657 B2 | 3/2011 | Shemesh et al. | |
| 8,269,167 B2 * | 9/2012 | deCecco et al. | 250/305 |
| 8,421,030 B2 | 4/2013 | Shadman et al. | |
| 2003/0080291 A1 | 5/2003 | Larson et al. | |
| 2003/0080292 A1 | 5/2003 | Watson et al. | |
| 2008/0197277 A1 | 8/2008 | Nasser-Ghodsi et al. | |
| 2009/0319196 A1 | 12/2009 | Schaller et al. | |

OTHER PUBLICATIONS

Bumgarner et al. "Automated peak identification applied to Auger electron spectroscopy", published by J. Vac. Sci. Technol. A, vol. 8, No. 3, May/Jun. 1990.

International Search Report and Written Opinion for application No. PCT/US2013/045441, dated Sep. 2, 2013.

* cited by examiner

| Elements | SNR | MP | TP | FP | KA Der 3s | TP | FP | KA Der 6s | TP | FP | KA Reg | TP | FP |
|---|---|---|---|---|---|---|---|---|---|---|---|---|---|
| None | 1000 | B Al Cl Ar Cu | - | 5 | Al Ca | - | 2 | None | - | 0 | None | - | 0 |
| Cu | 1000 | O F Cu | 1 | 2 | Cu Ni | 1 | 1 | Cu Ni | 1 | 1 | Cu | 1 | 0 |
| C Cu | 1000 | C Cu Ar | 2 | 1 | C Cu Ni | 2 | 1 | C Cu | 2 | 0 | C Cu | 2 | 0 |
| C Cu Si | 1000 | C Si Ar Cu | 3 | 1 | C Si Cu Ni B | 3 | 2 | C Cu Si | 3 | 0 | C Si Cu | 3 | 0 |
| None | 10 | Si N Cu | - | 3 | Si Fe Ge Mo Au | - | 5 | None | - | 0 | None | - | 0 |
| Cu | 10 | Cu Ar | 1 | 1 | B Cu Zr W | 1 | 3 | Cu | 1 | 0 | Cu | 1 | 0 |
| C Cu | 10 | C Al Ar Co | 1 | 3 | C Cu Al W Pb | 2 | 3 | C Cu | 2 | 0 | C Cu | 2 | 0 |
| C Cu Si | 10 | C N Al Si Ar Co Ni | 2 | 5 | C N Na Si Cu Fe Ta | 3 | 4 | C Cu Si | 3 | 0 | C Si Cu | 3 | 0 |
| None | 5 | N O Al Si S1 Cl Ni Cu | - | 8 | O Na | - | 2 | None | - | 0 | Hf | - | 1 |
| Cu | 5 | Cl Cu | 1 | 2 | Cu Ge Mn Ag Pb | 1 | 4 | Cu | 1 | 0 | Cu | 1 | 0 |
| C Cu | 5 | C Si Ar Cu | 2 | 2 | C Cu Ge | 2 | 1 | C Cu | 2 | 0 | C Cu | 2 | 0 |
| C Cu Si | 5 | C N Si P Co Cu | 3 | 3 | C Si Cu Zr Mn | 3 | 2 | C Si Cu | 3 | 0 | C Si Cu | 3 | 0 |
| None | 2 | O F Si Ar Ni | - | 5 | Ni Hf Au | - | 3 | None | - | 0 | None | - | 0 |
| Cu | 2 | N P Cu | 1 | 2 | Cu W | 1 | 1 | Cu | 1 | 0 | Cu | 1 | 0 |
| C Cu | 2 | C O F Cu | 2 | 2 | C Cu Ar | 2 | 1 | C | 1 | 0 | C Cu | 2 | 0 |
| C Cu Si | 2 | C N Si Cu | 3 | 1 | Cu Si Ag Cu Au Zr W | 3 | 4 | C Si | 2 | 0 | C Si Cu | 3 | 0 |
| None | 1 | N P Ni | - | 3 | Ga Fe Pt W | - | 4 | None | - | 0 | Si | - | 1 |
| Cu | 1 | F Al Si P S Ar Cu | 1 | 6 | Cu B Ta | 1 | 2 | Cu | 1 | 0 | Cu | 1 | 0 |
| C Cu | 1 | C Ni Cu | 2 | 1 | C Cu Ge W Pb | 2 | 3 | None | 0 | 0 | C Cu | 2 | 0 |
| C Cu Si | 1 | C N Si Cu | 3 | 1 | C Si As Sn Cu Ge Hf | 3 | 4 | None | 0 | 0 | C Si Cu | 3 | 0 |
| None | 0.5 | C O F | - | 3 | Fe Cr As W | - | 4 | None | - | 0 | Hf Si Al Ti Fe | - | 5 |
| Cu | 0.5 | N O Si P S Ar Cu | 1 | 6 | O Zr Cu Br As | 1 | 5 | None | 0 | 0 | Cu | 1 | 0 |
| C Cu | 0.5 | C Ar | 1 | 1 | C Cr Mn Ge B Pt | 1 | 5 | None | 0 | 0 | C Cu | 2 | 0 |
| C Cu Si | 0.5 | S | 0 | 1 | C Si P | 2 | 1 | None | 0 | 0 | C Si Cu | 3 | 0 |

AUGER ELEMENTAL IDENTIFICATION ALGORITHM

CLAIM OF PRIORITY

This application claims the benefit of priority of U.S. Provisional Application No. 61/658,494 to Mark Allen Neil, et al., entitled "AUGER ELEMENTAL IDENTIFICATION ALGORITHM" filed Jun. 12, 2012, the entire contents of which are herein incorporated by reference.

FIELD OF THE DISCLOSURE

The present disclosure relates to Auger Electron Spectroscopy (AES). More specifically, the present disclosure relates to methods and apparatus for decomposing an Auger electron spectrum into elemental and chemical components using multilinear regression techniques.

BACKGROUND

The demand for ever cheaper and lighter weight portable electronic devices has led to a growing need to manufacture durable, lightweight, and low cost electronic circuits including high density memory chips. The increasing complexity of electronic devices, and integrated circuits, coupled with the decreasing size of individual circuit elements, places ever more stringent demands on fabrication processes, particularly with respect to the resolution and accuracy of the fabrication patterns. The ability to fabricate on a nanometer scale guarantees a continuation in miniaturization of functional devices.

Micro-fabrication techniques can produce structures having features on the order of nanometers. Micro-fabrication is used in a wide variety of applications, such as the manufacturing of integrated circuits (i.e. semiconductor processing), biotechnology, optical technology, mechanical systems, and micro-electro-mechanical systems ("MEMS").

Micro-fabrication is typically a multi-step process involving the patterned deposition or removal of material from one or more layers that make up a finished device. Micro-fabrication is sensitive to the presence of contaminant particles. In micro-fabrication it is common to inspect a substrate for the presence of contaminants between process steps. As the size of micro-fabricated features decreases, smaller and smaller contaminant particles and films can affect device yield. A number of tools have been developed for detecting contaminant particles. Inspection tools, such as a scanning electron microscope (SEM) are commonly used to inspect a partially fabricated device or wafer containing multiple devices for defects. For certain cases, it may be sufficient to image the defects, e.g., with the SEM and analyze the image to characterize the defects. But for many cases, once defects have been detected it is important to characterize the material composition.

Instrumentation for use in spectroscopic elemental analysis makes use of electrons, ions, or X-rays which are emitted from a substance after being bombarded or irradiated with electrons or ions from a source such as an electron gun. Energy Dispersive X-ray analysis (EDX) is a technique in which an electron beam strikes the surface of a conducting sample. The energy of the beam is typically in the range 5-20 kilo electron-volts (keV). This causes X-rays to be emitted from the region of impact of the electrons with the sample. The energy of the X-rays emitted depends on the material under examination. For EDX, the X-rays are generated in a region of several hundred nanometers to several microns in depth. For sufficiently large defects, EDX may have adequate sensitivity and spatial resolution. Unfortunately, for very small defects EDX may not have the sensitivity to characterize them.

Another charged particle spectroscopy technique is known as Auger electron spectroscopy (AES). Unlike EDX which detects X-rays, AES detects secondary electrons that are emitted with an energy characteristic of the material of the surface. Auger data is obtained with an electron detection system having an electron energy analyzer, such as a cylindrical mirror analyzer (CMA), hemispherical sector analyzer (HSA), a hyperbolic field analyzer, or an S-curve analyzer.

An example of a hyperbolic field analyzer that may be used to acquire an Auger electron spectrum is disclosed in commonly assigned U.S. Pat. No. 7,635,842 to Mehran Nasser-Ghodsi et al., entitled "METHOD AND INSTRUMENT FOR CHEMICAL DEFECT CHARACTERIZATION IN HIGH VACUUM" filed Feb. 15, 2008, the entire contents of which are herein incorporated by reference.

An example of an S-curve analyzer that may be used to acquire an Auger electron spectrum is disclosed in commonly assigned U.S. Pat. No. 8,421,030 to Khashayar Shadman et al., entitled "CHARGED-PARTICLE ENERGY ANALYZER" filed Mar. 17, 2011, the entire contents of which are herein incorporated by reference.

Acquiring the Auger electron input spectrum with the electron energy analyzer involves bombarding the target sample with a stream of electrons from some source, such as an electron gun, and detecting electron energies emitted therefrom. Upon incidence of the electrons the target material gives off a variety of emissions, including X-rays, secondary electrons, and backscattered primary electrons from the source. The emissions include Auger electrons (a particular class of secondary electrons) in the manner which is well known in the literature. Auger electron spectroscopy is a surface analytical technique because the energies of the electrons emitted are typically in the range of 50 eV to 3 keV, and at this energy they cannot escape from more than a few nanometers deep in the surface (of course, the higher the energy, the thicker the layer from which they can escape).

The emitted electrons are plotted as spectrum that is a function of energy to obtain the input spectrum to be analyzed by the particular Auger electron spectroscopy analytical technique. This input signal includes both a broad background spectrum of secondary electrons as well as one or more Auger spectra for the particular elements present in the target sample. This input spectrum can be analyzed using an appropriate Auger electron spectroscopy analytical technique in order to chemically characterize the target material based on the Auger spectra present in the signal.

Characterizing the surface of the target material may include determining the type of elements present in a spectrum based on the characteristic Auger spectra present in the input spectrum. A general goal of Auger electron spectroscopy analytical technique is to isolate the relevant Auger spectra from the spectral data, which may be a noisy signal that includes both broad background spectrum corresponding to non-Auger secondary electron energies and noise produced by the particular electron detection system used to acquire the data.

However, there are several drawbacks with traditional AES analytical techniques. For one, they suffer from poor performance when attempting to analyze a noisy signal, which may make it difficult to distinguish Auger electron transition peaks in the derivative signal. Moreover, traditional techniques do not handle peak ambiguity well, where different elements and/or chemicals have similar transition peak locations or overlapping Auger spectra in the input spectrum. Additionally, traditional techniques suffer from poor performance with even trivial spectral shifts, such as may be due to chemical composition or calibration issues.

To obtain a good quality signal, i.e. one with a high signal to noise ratio (SNR), the target sample may be placed in an Ultra High Vacuum (UHV), typically about $10^{-10}$ Torr to $10^{-9}$ Torr. However, the design complexity of UHV systems and slower operational cycle prevents rapid analysis of defects in production-scale substrate processing, which tend to operate at high vacuum, e.g., about $10^{-7}$ to about $10^{-6}$ torr. Auger spectroscopy can be conducted faster and in a high vacuum environment of a production environment, but the process may produce a lower quality spectral input signal having a low SNR, resulting in poor identification performance when using traditional Auger analytical techniques It is within this context that aspects of the present disclosure arise.

SUMMARY

One aspect of the present disclosure is a method of Auger spectral analysis of an input spectrum, the input spectrum including an Auger spectrum, the method including: conditioning the input spectrum to generate a normalized input spectrum; determining statistical correlation between the normalized input spectrum and stored elemental spectral signatures; and characterizing species in the input spectrum from the statistical correlation, wherein conditioning the input spectrum includes estimating a background signal of non-Auger electrons in the input spectrum and subtracting the estimated background signal from the input spectrum.

In some implementations, the estimated background signal is a convex envelope of the input spectrum and estimating the background signal includes using a convex hull algorithm to calculate the convex envelope.

In some implementations, determining statistical correlation includes performing multilinear regression on the normalized input spectrum against the stored elemental spectral signatures.

In some implementations, conditioning the input spectrum includes filtering the input spectrum to remove noise from the input spectrum.

In some implementations, filtering the input spectrum includes applying a Savitzky-Golay smoothing filter to the input spectrum.

In some implementations, filtering the input spectrum includes applying a Gaussian filter to the input spectrum.

In some implementations, filtering the input spectrum includes applying a binomial filter to the input spectrum.

In some implementations, filtering the input spectrum includes applying a boxcar filter to the input spectrum.

In some implementations, the method includes acquiring the input spectrum, wherein acquiring the input spectrum includes directing a beam of electrons at a target and determining an energy spectrum of secondary electrons emitted from the target with an electron detection system.

In some implementations, the target is a defect on a semiconductor wafer.

In some implementations, the electron detection system is included in a Metrology of review tool.

In some implementations, conditioning the input spectrum includes subtracting a reference spectrum from the input spectrum.

In some implementations, the method includes acquiring the input spectrum, wherein acquiring the input spectrum includes directing a beam of electrons at a defect on a semiconductor wafer and determining an energy spectrum of secondary electrons emitted from the defect with an electron detection system; and acquiring the reference spectrum, wherein acquiring the reference spectrum includes directing a beam of electrons at target on the semiconductor wafer that does not have a defect and determining an energy spectrum of secondary electrons emitted from the target with the electron detection system.

In some implementations, characterizing species includes identifying elements in the input spectrum.

In some implementations, characterizing species includes determining concentrations of the identified elements.

In some implementations, characterizing species includes determining confidence levels of the identified elements.

Yet another aspect of the present disclosure is a system having: a processor unit; a memory unit coupled to the processor unit; a plurality of elemental spectral signatures embodied in the memory unit; and program instructions embodied in the memory unit an executable by the processor unit, wherein execution of the program instructions by the processor unit causes the processor unit to implement a method of Auger spectral analysis of an input spectrum, the input spectrum including an Auger spectrum, the method including: conditioning the input spectrum to generate a normalized input spectrum; determining statistical correlation between the normalized input spectrum and the elemental spectral signatures; and characterizing species in the input spectrum from the statistical correlation, wherein conditioning the input spectrum includes estimating a background signal of non-Auger electrons in the input spectrum and subtracting the estimated background signal from the input spectrum.

In some implementations, the system includes an electron detection system, wherein the method further includes acquiring the input spectrum, wherein acquiring the input spectrum includes directing a beam of electrons at a target and determining an energy spectrum of secondary electrons emitted from the target with the electron detection system.

In some implementations, the electron detection system is equipped in a Metrology of review tool.

Yet another aspect of the present disclosure is a non-transitory computer readable medium having program instructions embodied therein, wherein execution of the program instructions by a processor unit causes the processor unit to perform a method of Auger spectral analysis of an input spectrum, the input spectrum including an Auger spectrum, the method including: conditioning the input spectrum to generate a normalized input spectrum; determining statistical correlation between the normalized input spectrum and stored elemental spectral signatures; and characterizing species in the input spectrum from the statistical correlation, wherein conditioning the input spectrum includes estimating a background signal of non-Auger electrons in the input spectrum and subtracting the estimated background signal from the input spectrum.

BRIEF DESCRIPTION OF THE DRAWINGS

The teachings of the present disclosure can be readily understood by considering the following detailed description in conjunction with the accompanying drawings, in which.

DETAILED DESCRIPTION

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

INTRODUCTION

As used herein, an element's "spectral signature" refers to some or all of the element's characteristic Auger spectrum across a range of electron energies. In particular, while an elemental "spectral signature" as defined herein is not necessarily an entire Auger spectrum of an element, a "spectral signature" includes at least some of an element's characteristic Auger spectral data across a range of energies, not just a characteristic peak location. Consequently, elemental identification algorithms according to aspects of the present disclosure do not necessarily require data for a full range of energies for reference spectra. Aspects of the present disclosure may be implemented in cases where the reference spectrum that is used includes only a small energy window of a larger reference spectrum.

Figure 1:
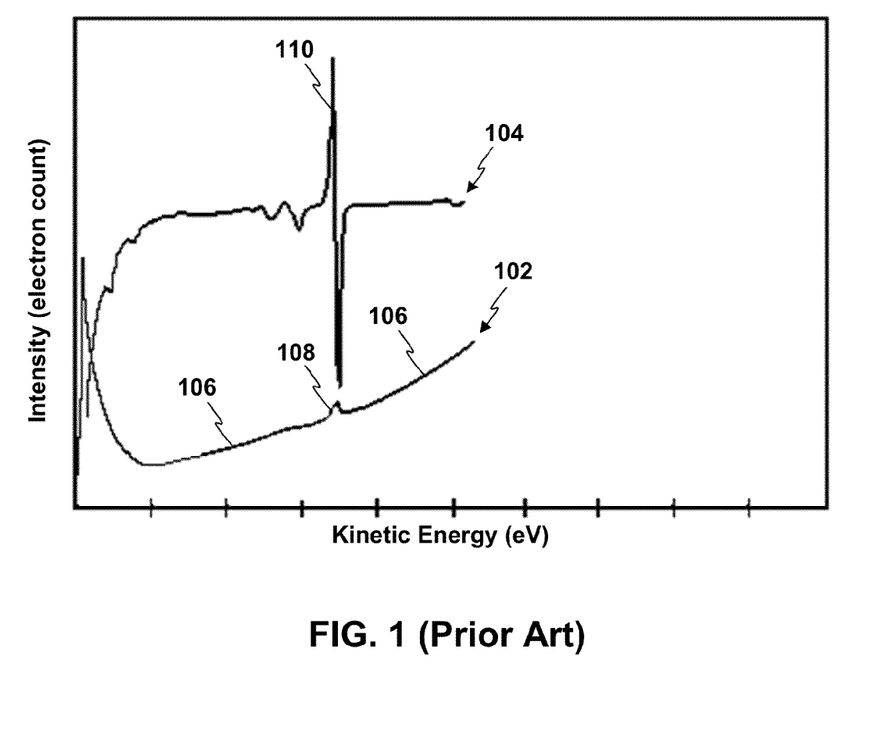
FIG. 1 is a spectrum depicting an Auger electron input spectrum and its derivative according to a traditional Auger analytical technique.

Traditional Auger spectroscopy analytical techniques typically attempt to isolate the Auger data from the background spectrum by taking the derivative of the input signal and searching for transition peaks at known energies for different elements and chemicals, wherein these transition peaks in the derivative signal correspond to the Auger electrons of the input spectrum. The location (i.e. energy) of these transition peaks may be determined by searching for peaks in the derivative signal having a magnitude above some threshold. An illustrative example of an input spectrum 102 for Auger electron spectroscopy and its corresponding derivative 104 is depicted in FIG. 1. The Auger spectral data includes both a broad non-Auger background spectrum 106 extending across the length of the input spectrum 102 and an Auger spectrum 108 localized at a particular energy of the input spectrum 102. In order to isolate the Auger data from the background signal and identify chemical or elemental species based on the Auger peak locations, many traditional analytical techniques involve taking the derivative 104 of the input spectrum 102 and identifying the at which energy the Auger electrons were emitted based on the location of spikes 110 in the derivative signal, which correspond to transition peaks in the original signal.

According to aspects of the present disclosure, elemental and chemical species in an Auger input spectrum can be characterized using statistical correlation techniques. The characteristic background signals corresponding to non-Auger secondary electrons can be estimated and the estimated signal can be subtracted from the Auger input spectrum in order to isolate the Auger spectra in the underlying input signal. Identification techniques can include a background signal estimation algorithm that can be applied across different Auger input spectra having various sample and system dependent background signals. Multilinear regression (sometimes known as "multiple linear regression") can be used to determine statistical correlation between stored elemental spectral signatures and the normalized Auger input spectra with the background signal removed.

According to aspects of the present disclosure, in Auger electron spectroscopy any input spectrum can be considered to be a linear combination of Auger elemental signatures, a background signal of non-Auger electrons, and noise generated from the electron detection process. For example, $S_{input} = k_1 Cu + k_2 Fe + S_{background} + S_{noise}$, where $S_{input}$ is an Auger input signal having Copper (Cu) and Iron (Fe) Auger spectra, in addition to a broad non-Auger background signal $S_{background}$ and signal noise $S_{noise}$. Regression can be used to find $k_1$ and $k_2$ in the above example. Moreover, it is reasonable to expect the regression coefficients $k_1$ and $k_2$ to be linearly dependent to composition. Accordingly, the regression coefficients $k_1$ and $k_2$ may be used to determine relative concentrations of the elements and/or chemical compositions present in the sample from which the Auger input spectrum was obtained.

The background signal $S_{background}$ may negatively impact identification of elements as well as determination of their concentrations as it distorts the underlying Auger data of interest. Moreover, the background signal of each input spectrum may be different based on various sample and detection system specific characteristics. According to aspects of the present disclosure, in some implementations this background signal can be accurately estimated automatically and across different input spectra in a manner that does not require human intervention to account for differences in the input spectra.

SPECIFIC EMBODIMENTS

Figure 2:
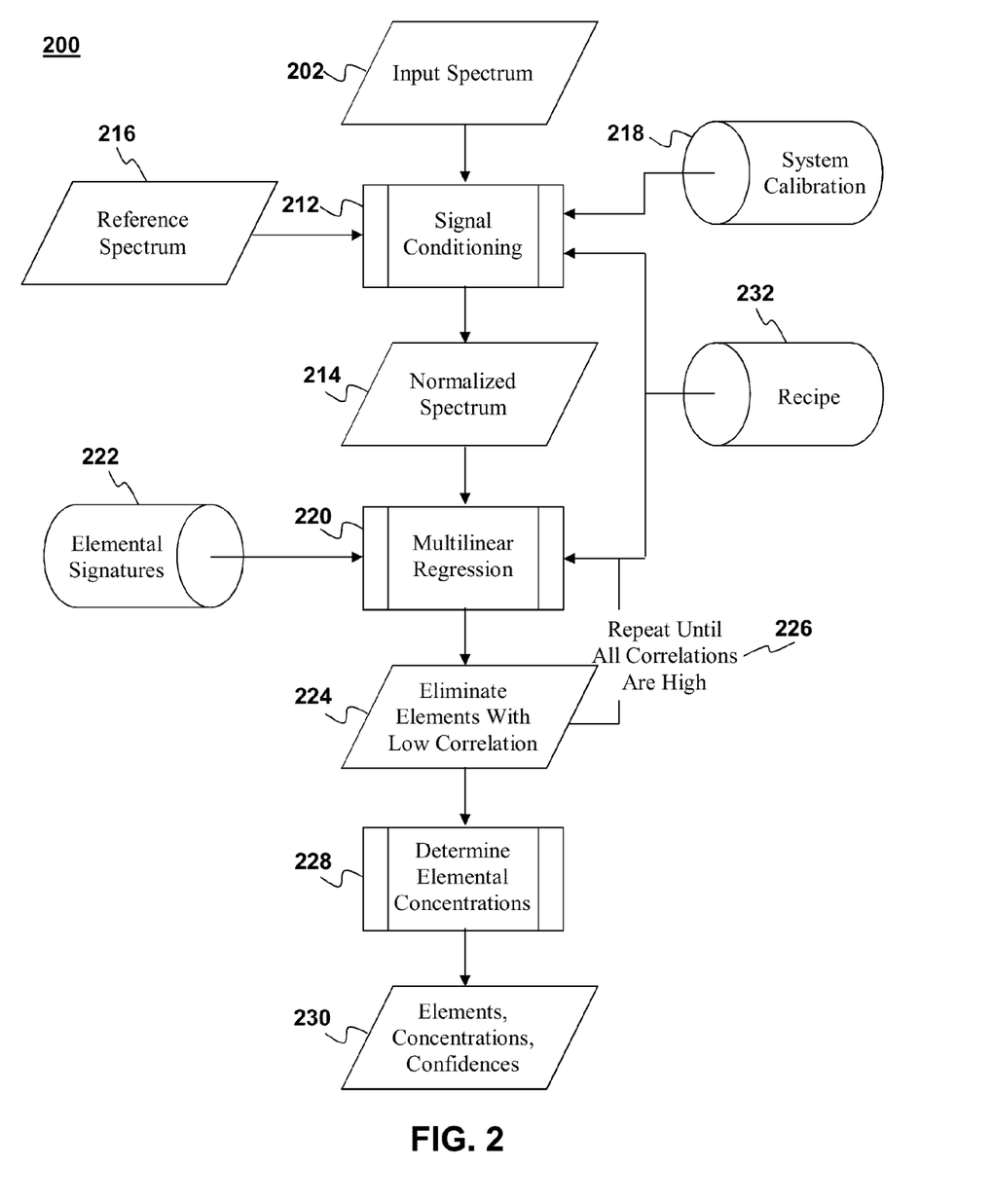
FIG. 2 is a flow diagram depicting a method of decomposing an Auger electron input spectrum into elemental and chemical components according to various aspects of the present disclosure.

An illustrative implementation of the present disclosure is depicted in FIG. 2. The illustrated implementation depicts a method 200 for analyzing Auger spectral data in accordance with various aspects of the present disclosure.

Although not shown in the figure, the method 200 may include acquiring Auger data for the input spectrum 202 by bombarding a target sample with energetic electrons and detecting secondary electrons (including Auger electrons). The Auger data may be gathered with an electron detection system that includes an electron energy analyzer. By way of example, and not by way of limitation, the electron energy analyzer may be a cylindrical mirror analyzer (CMA), hemispherical sector analyzer (HSA), a hyperbolic field analyzer, or an S-curve analyzer. The target material to be analyzed may be a semiconductor wafer having a defect, and the electrons may be directed at the defect in order to characterize the chemical and elemental species present in the defect. In some implementations, the electron detection system may be located in a semiconductor fabrication facility (fab). The electron detection system may be a standalone unit in the fab or may be integrated into a tool. For example, the electron detection system may be integrated into a semiconductor analysis tool, such as, e.g., a metrology of review tool or an inspection tool.

Once the input spectrum 202 is obtained, the method 200 may include conditioning the input signal at 212 in order to produce a normalized spectrum 214. Conditioning the signal at 212 may include estimating a background spectrum of the input signal 202 and subtracting the estimated background signal from the input spectrum 202. Calculating the estimate of the background signal may be performed in a variety of ways. By way of example, and not by way of limitation, calculating the estimate of the background signal may be performed by using a convex hull algorithm to calculate a convex hull of the data set making up the input spectrum, or by calculating the "minimum slope fit" of the input signal, in accordance with aspects of the present disclosure.

Signal conditioning 212 may also optionally include subtracting a reference spectrum 216 in order to eliminate Auger spectra from the input spectrum 202 that are not of interest. This may include obtaining a spectrum with the electron detection system from nearby the target sample, wherein this nearby location of the material is presumed not to have all of the elements found in the target sample from which the input spectrum 202 was gathered. This reference spectrum 216 may be subtracted from the input spectrum 202 in order to remove one or more Auger spectra that are not of interest from the input signal 202. In an implementation in a semiconductor fab, this may include driving electrons at a portion of a wafer that does not have the defect being characterized, and subtracting this gathered reference spectrum from the input spectrum in order to obtain only that Auger data related to contaminants in the defect. This may optionally be used to optimize the method 200 and avoid unnecessary calculations.

Signal conditioning 212 may also optionally include filtering the input spectrum in order to smooth the signal and eliminate noise. By way of example, and not by way of limitation, filtering the input spectrum 202 utilizing a Savitzky-Golay, Binomial, Gaussian, or Boxcar filter. As noted above, Auger electron production and data gathering is inherently a noisy process. In implementations, signal conditioning 212 may include filtering the input spectrum 202 to remove noise and improve identification. However, filtering to reduce may also reduce the signal intensity and decrease identification success in a different way. Accordingly, care may be taken to avoid over filtering the input spectrum 202. In some implementations, filtering of the input spectrum 202 may be omitted entirely from the signal conditioning to produce the normalized input spectrum. Moreover, where filtering is used to de-noise the input spectrum, similar or identical filtering as is used on the input spectrum 202 may be used on the stored elemental spectral signatures 222 in order to ensure accurate correlation results.

Signal conditioning 212 may also include calibration based on system specific calibration data 218, such as, e.g., subtracting a measured electronic dark current curve from the input spectrum 202. The dark current curve is basically a spectrum obtained with the same system used to generate the input spectrum 202 but without bombarding the target with electrons to produce secondary electrons. In some implementations the dark current may be expected to be a low frequency curve and may automatically be removed by the other methods of background removal. Accordingly, this step may be omitted for simplicity.

Signal conditioning 212 may also include resampling the signal at a different bin size, e.g., to eV, and normalizing the amplitude. It is noted that energy bin size is different from energy resolution. Typically one chooses a bin size of about one half of the resolution. Signal conditioning 212 may also include clipping the input signal to particular range of energies of interest. By way of example, and not by way of limitation, this may include clipping the input spectrum to a range of 100-2050 eV.

Once the normalized spectrum 214 is obtained, the method 200 may include using non-negative multilinear regression at 220 to correlate one or more spectra in the normalized spectrum 214 with one or more characteristic Auger spectra contained in a database of stored elemental spectral signatures 220. Because each element generally has a characteristic Auger spectrum, multilinear regression 220 may be used to determine statistical correlation between such characteristic Auger spectra 222 and one or more portions of the normalized spectrum 214 in order to determine the presence of elements and chemical species present in the surface of the target sample from which the input spectrum 202 was obtained. A database of these elemental spectral signatures 222 may include as many elements as desired and whatever species are of interest for characterizing the particular target sample from which the input spectrum 202 was obtained. Likewise, multilinear regression 220 may be used to determine a correlation between the normalized input spectrum 214 and some or all of the elemental spectral signatures depending on which elements stored in the database are of interest.

The multilinear regression 220 may be performed iteratively by eliminating elements with low correlation at 224 and repeating the multilinear regression until all correlations are sufficiently high at 226. This may include eliminating elements which are unlikely to be "real," i.e., those that have a low probability of being present on the sample or those that have small correlation coefficients, e.g., about 10% or less. This process can include finding elemental matches sequentially, with each selection minimizing residual error, and iterating until an exit criterion is met or the maximum matches is reached. Eliminating elements with low correlation at 224 can include eliminating elements with large p-values and small correlation coefficients.

The method 200 may then include determining elemental concentration at 228 based on statistical correlation determined from the iterative multilinear regression. The elemental concentrations at 228 may typically correspond to the multilinear coefficients output from the iterative multilinear regression. The coefficients may be normalized to sum up to 1.0 (i.e., 100% composition) so that the composition values or concentrations are the regression coefficients. Accordingly, iterative multilinear regression may be used to directly output elements and their respective concentrations at 228 that are present in the input spectrum 202 that is under test. The results 230 of the illustrative method 200 may include elements and corresponding concentrations, as well as confidences, such as, e.g., a confidence factor of 0-100% for each identified element, indicating how likely the determined elements and concentrations are to be true. The confidence factor may be, e.g., (100*(1−p-value) %).

Although not pictured, the method 200 may also include updating the database of stored spectral signatures 222 in order to use correlation results to improve the accuracy of the stored signatures for future identification.

The method 200 may be performed in accordance with a recipe 232 defining certain parameters. By way of example, and not by way of limitation, the recipe parameters may include filter steps and parameters for signal conditioning, as well as a list of the elements of interest for elemental identification. The method 200 may include only elements of interests in the search for correlations between the stored signatures. In some implementations, certain parameters in the recipe used for identification may be input by a user prior to a particular execution of the method 200.

As noted above, with Auger electron spectroscopy, an input spectrum will generally include one or more Auger electron spectra containing the relevant data of interest for characterizing chemical and elemental species, as well as a background signal corresponding to non-Auger secondary electrons emitted from the target sample. This background spectrum is generally dependent on the particular target sample and electron detection system used to obtain the data for the input spectrum, and may negatively impact identification and calculation of concentrations of the species present in the input spectrum. Accordingly, the background signal should be removed from the input spectrum in order to identify species and calculate concentrations in the spectrum under test.

Traditional techniques typically involve isolating the Auger data from the background signal by taking the derivative of the input spectrum, as described above with reference to FIG. 1. However, this suffers from several drawbacks. In implementations of the present disclosure, the background signal can be removed by first calculating an estimate of the background signal from the input spectrum being analyzed, then removing this estimated background signal from the input spectrum.

Figure 3A:
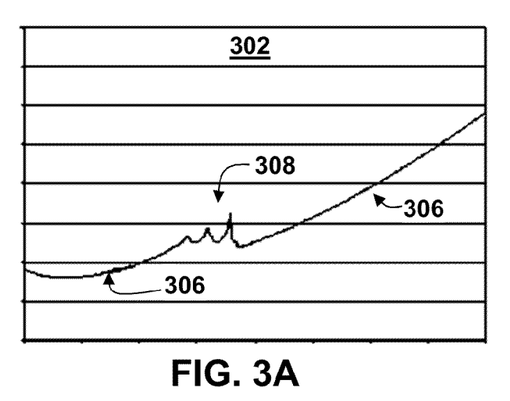
FIGS. 3A-3C are spectra depicting estimation and subtraction of a background signal from an Auger electron input spectrum according to various aspects of the present disclosure.
Figure 3B:
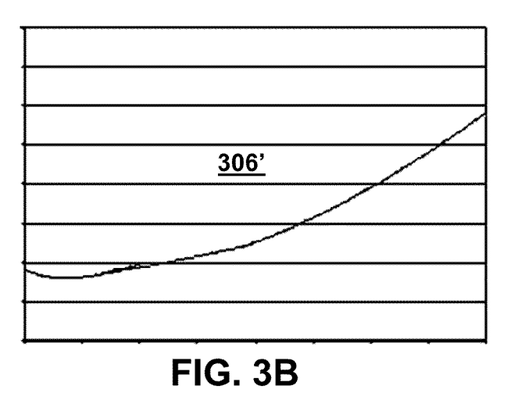
Figure 3C:
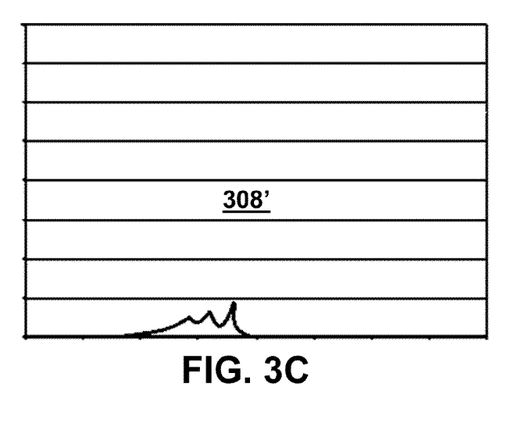

FIGS. 3A-3C illustrate various aspects estimating a background signal from an input spectrum and removing the background signal to produce a normalized input spectrum in accordance with various aspects of the present disclosure.

An illustrative Auger electron spectroscopy input spectrum 302 is depicted in FIG. 3A. The illustrative input spectrum 302 includes a Copper (Cu) signature Auger spectrum 308 against a broad background spectrum 306 as sampled from a target material with an Auger electron detection system. It is noted that the illustrated input spectrum 302 is a signal having very low noise and only one elemental Auger spectrum 308 for purposes of illustration only.

An estimated background spectrum 306' of the input spectrum 302 is depicted in FIG. 3B. This estimated background spectrum 306' may be subtracted from the input signal 302 in order to isolate the Auger spectrum 308' in the input signal 302. In some implementations, the isolated Auger spectrum 308' may correspond to a normalized input spectrum for determining correlation to stored elemental spectral signatures. In other implementations, signal conditioning may include various other preprocessing steps, such as, e.g., denoising the signal with a filter and clipping to a range of energies of interest before generating the normalized input spectrum.

According to aspects of the present disclosure, the background spectrum can be estimated in a manner that recognizes certain characteristics of Auger input signals that are independent of the particular target sample or detection system used to gather the spectral data. In implementations of the present disclosure, techniques for Auger spectral analysis can employ an algorithm that leverages these truisms to calculate accurate estimates of the background signal across different input spectra under test, wherein each spectrum under test may different have tool and sample dependent characteristic background signals. The estimated background signal can then be subtracted from the input spectrum without significantly distorting the Auger spectra of interest in order to accurately determine correlations with stored elemental spectral signatures.

According to one implementation, an estimate of the characteristic background signal can be calculated with a convex hull algorithm to calculate a convex hull of an input spectrum. As is known in mathematics, a convex hull (sometimes called a convex envelope) of a set of points is the smallest convex set that contains X. A set of points is said to be convex if contains the line segments that connect each pair of points in the set. To visualize this, imagine stretching a rubber band around a set of discrete points that makes up an input spectrum. This technique recognizes the fact that, specifically with Auger electron spectroscopy, the background spectra of non-Auger secondary electrons is characteristically in the form of a generally upwardly curving or bowl shaped spectrum. Moreover, the one or more Auger spectra in the input spectrum are positive additions to the characteristic background curve. In other words, this technique recognizes that the underlying background signal of non-Auger electron energies generally corresponds to convex envelope of the data points, while Auger electrons in the input signal are concave additions to the underlying characteristic background curve. Accordingly, a convex hull algorithm can be used to calculate this convex envelope of each input spectrum and leverage these truisms of Auger electron spectroscopy. This same convex hull algorithm can be applied across different input spectra having various sample or system dependent characteristics in order to compute accurate estimates of the background signal that are specific to each input spectrum.

According to another implementation, estimating the background spectrum can be calculated by what will be referred to herein as calculating the "minimum slope fit" of the input spectrum. This type of algorithm is different from a convex hull, which does not generally do a fit. Starting at the lowest energy point, or a predetermined low energy point, in the input spectrum, the algorithm can search for the next highest energy point which minimizes the slope of the line connecting the points. This can be repeated until all points have been traversed. This approach takes advantage of the fact that the background signal is always either monotonically decreasing or monotonically increasing. This technique also takes advantage of the fact that the elemental signatures, i.e., the Auger spectra of interest in the input signal, are positive additions to the background signal.

Figure 3D:
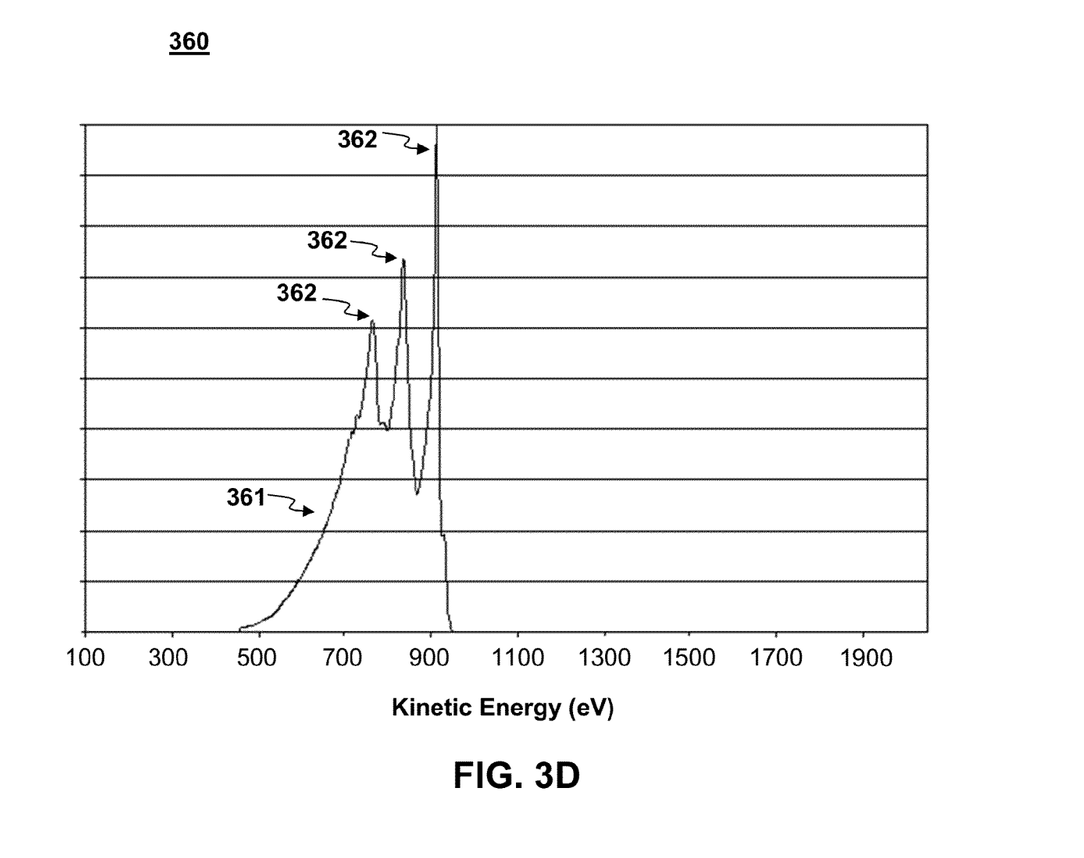
FIG. 3D depicts an elemental signature spectrum according to various aspects of the present disclosure.

An illustrative elemental spectral signature 360 is depicted in FIG. 3D in order to illustrate various aspects of the present disclosure. In this example, the spectral signature 360 is a characteristic Auger spectrum for Copper (Cu).

The sharp but weak features between 600 and 1000 eV correspond to the Cu LMM Auger electrons. Only a fraction of the Auger electrons escape from the surface of the target without being inelastically scattered. The majority of the Auger electrons are scattered one or more times and contribute to a broad inelastic tail 361 on the low kinetic energy side of the Auger peaks 362.

Referring to FIG. 3D, one can clearly see this effect of a sharp peak and a slowly decaying tail for each of the LMM components 362 of the signature. In some implementations, the combination of the peak portions 362 and the tail portions 361 can be used to improve identification and utilize a broad spectrum of characteristic data for each element. In high-noise situations, the presence of a peak might simply be noise. But it is highly unlikely to observe the peak-tail "saw-tooth" signal in noise alone. Accordingly, in contrast to traditional approaches that simply look for peak transitions in a derivative signal, implementations of the present disclosure can search for stored kernels.

According to aspects of the present disclosure, a database of stored spectral signatures can include correlation kernels that contain all or only a portion of the characteristic Auger spectrum for a particular element, such as, e.g., a correlation kernel of some or all of the spectrum 360 depicted in FIG. 3D. The width of the kernel or amount of spectral information present in the kernel can be varied as desired. Because the entire width of a characteristic Auger spectrum may overlap with other elements, it may be desirable to use only a portion of the signature spectrum as a correlation kernel so that identification result are improved for input spectrum containing multiple elements.

In some implementations, the stored spectral signatures may include correlation kernels that include the entire sharp transition towards higher energies of each peak and some portion of the inelastically scattered ramp up towards lower energies. The portion used may be chosen in such a way that it adds useful data to the correlation without occluding a neighboring peak for a different element, and the portion chosen may be different for different elements.

Figure 4:
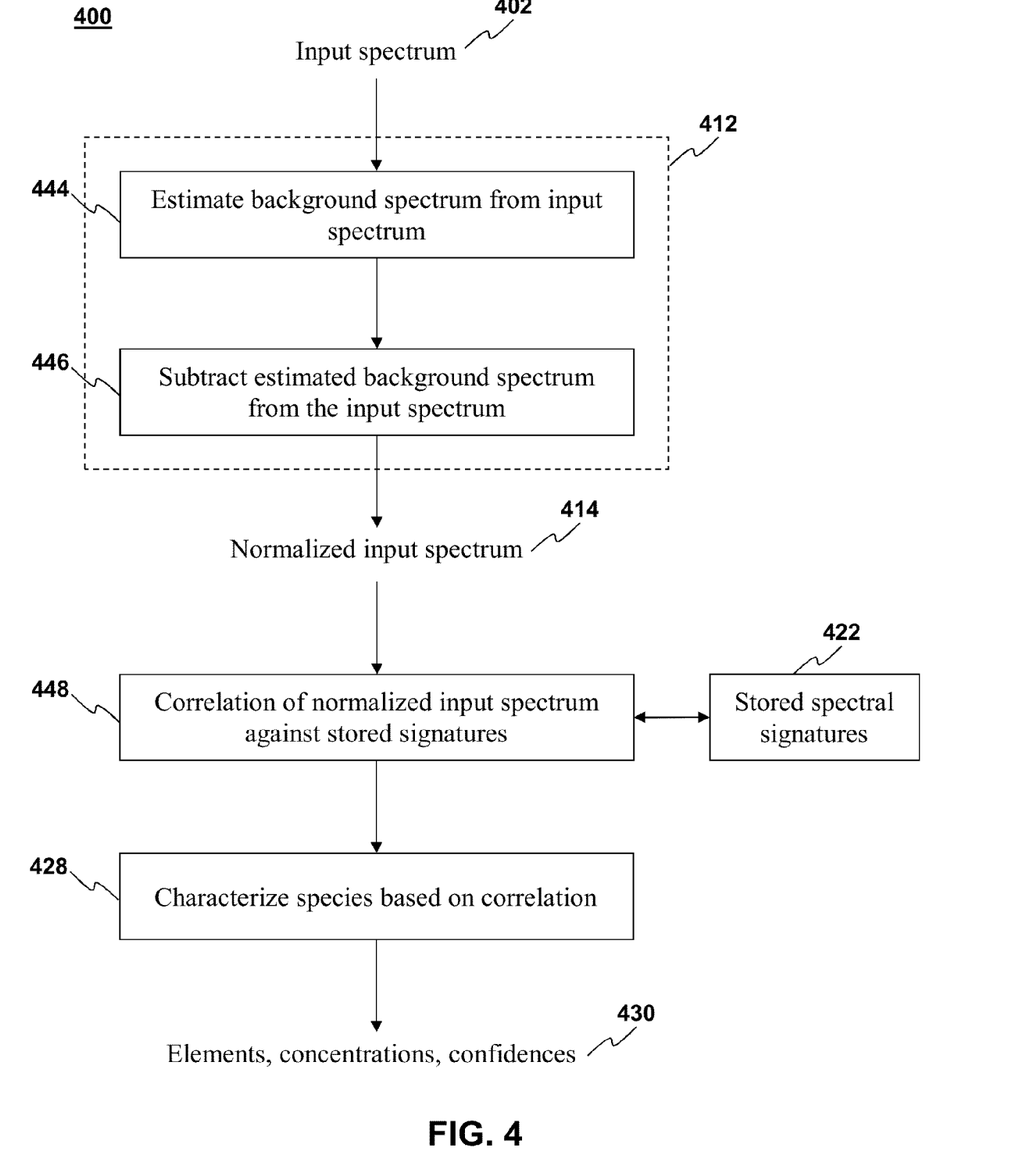
FIG. 4 is a flow diagram depicting a method of decomposing an Auger electron input spectrum into elemental and chemical components according to various aspects of the present disclosure.

Another aspect of the present disclosure is depicted in the flow diagram FIG. 4, which illustrates a method 400 for performing Auger spectral analysis. The method 400 utilizes iterative multilinear regression in order to characterize chemical and elemental species present in an input spectrum taken from a target material under test. The input spectrum may be obtained using an Auger electron detection system that includes an electron analyzer.

In the illustrated method 400, an input spectrum 402 containing Auger spectral data is first conditioned at 412 to generate a normalized input spectrum 414. Conditioning the input spectrum at 412 includes estimating a background spectrum at 444 corresponding to non-Auger electron energies in the input spectrum from the input signal 402. Estimating the background spectrum at 444 may be performed in accordance with various aspects of the present disclosure. By way of example, and not by way of limitation, calculating the estimate of the background signal may be performed by using a convex hull algorithm to calculate a convex hull of the data set making up the input spectrum, or by calculating the "minimum slope fit" of the input signal, in accordance with various aspects of the present disclosure.

In the method 400, signal conditioning at 412 also includes subtracting the estimated background spectrum at 446 in order to eliminate non-Auger electrons from the energy spectrum. Signal conditioning at 412 results in a normalized input spectrum 414.

The normalized input spectrum 414 can be correlated with stored elemental spectral signatures 422 as indicated at 448. Correlating the normalized input spectrum at 448 can include performing iterative multilinear regression on the normalized input spectrum 414 against stored elemental spectral signatures 422 to determine statistical correlation therebetween.

The correlation determined at 448 between the normalized input spectrum 414 and the stored elemental signatures 422 can be used to characterize chemical and elemental species present in the input spectrum 402. The statistical correlation can be used to identify elements present in the input spectrum that match elements' stored spectral signatures in the data 422. The correlation can also be used to determine corresponding concentrations of the identified elements, such as, e.g., based on multilinear regression coefficients. Accordingly, characterizing the species based on the statistical correlation at 428 may include identifying elements, corresponding concentrations, confidence levels, or any combination thereof at 430.

Figure 5:
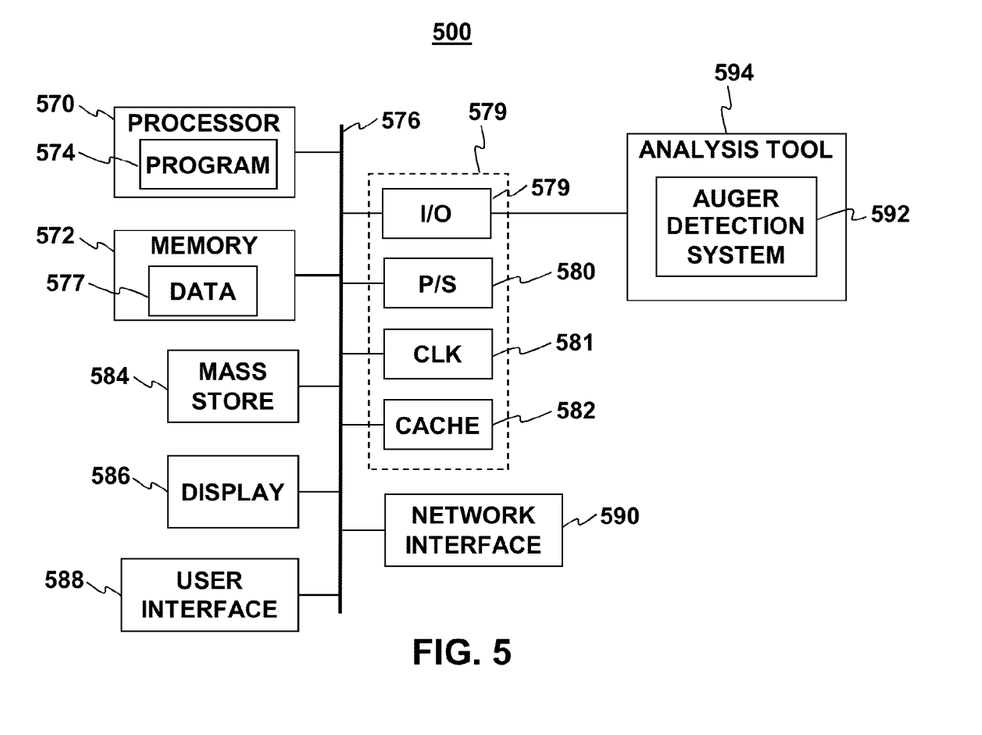
FIG. 5 is a block diagram of a system for performing Auger spectral analysis according to various aspects of the present disclosure.

FIG. 5 depicts a system 500 for performing Auger electron spectroscopy analysis according to various aspects of the present disclosure.

The system 500 may include a processor unit 570. By way of example, the processor unit 570 may include one or more processors, which may be configured according to different well known architectures, such as, e.g., a dual-core, quad-core, multi-core, or processor-coprocessor architecture. The system 500 may also include a memory unit 572 (e.g., RAM, DRAM, ROM, and the like). The processor unit 570 may execute a program 574, portions of which may be stored in the memory 572, and the processor may access the memory via a data bus 576. The memory unit 572 may include data 577, and the processor unit 570 may utilize the data 577 in implementing the program 574. The data 577 may include signal data, such as one or more input spectra obtained from an Auger electron detection system. The program 574 may include instructions that, when executed, perform Auger electron analysis to characterize elemental and chemical species of a target sample in accordance with various aspects of the present disclosure. The data 577 may also include one or more stored spectral signatures for one or more elements of interest.

The system 500 may also include well-known support circuits 578, such as input/output (I/O) circuits 579, power supplies (P/S) 580, a clock (CLK) 581, and cache 582, which may communicate with other components of the system, e.g., via the bus 576. The system 500 may optionally include a mass storage device 584 such as a disk drive, CD-ROM drive, tape drive, flash memory, or the like, and the mass storage device 584 may store programs and/or data. The system 500 may also optionally include a display unit 586. The display unit 586 may be in the form of a cathode ray tube (CRT), flat panel screen, touch screen, or other device that displays text, numerals, graphical symbols, or other visual objects. The system 500 may also include a user interface 588 to facilitate interaction between the system 500 and a user. The user interface 588 may include a keyboard, mouse, light pen, control pad, or other device.

A user, such as, e.g., a fab engineer, may able set up Auger acquisitions and/or identification parameters in a recipe with the user interface 588. The display unit 586 may form a portion of the user interface 588 via touchscreen display unit. The user interface 588 may include a graphical user interface (GUI) that can be displayed on the display unit 586 in order to facilitate user interaction with the system 500. The system 500 may include a network interface 588, configured to enable the use of Wi-Fi, an Ethernet port, or other communication methods. The network interface 590 may incorporate suitable hardware, software, firmware or some combination thereof to facilitate communication via an electronic communications network. The network interface 590 may be configured to implement wired or wireless communication over local area networks and wide area networks such as the Internet. The controller 500 may send and receive data and/or requests for files via one or more data packets over a network. These components may be implemented in hardware, software, firmware, or some combination thereof.

The system 500 may be configured to receive spectral data for Auger analysis, which may form a portion of the data 577. The system may also optionally be equipped to gather the Auger data with an electron detection system 592. The electron detection system 592 may include an electron source, such as, e.g., an electron gun that drives an electron beam to a target material to produce electron emissions that include Auger electrons. The electron detection system 592 may also include an electron energy analyzer, such as, e.g., an S-curve analyzer, a hyperbolic field analyzer, a cylindrical mirror analyzer (CMA), or other analyzer suitable for obtaining an electron energy spectrum that can be used in Auger electron spectroscopy. In a CMA, electrons pass through an electric field established by a voltage difference between two concentric cylinders. Electrons with the right energy pass between the cylinders to an electron detector. To obtain a spectrum, the voltage between the cylinders is changed and the signal from the detector is plotted as a function of the voltage difference. In an S-curve analyzer or hyperbolic field analyzer, electrons passing through an electric field take slightly different paths and land at different locations depending on their energies. Such analyzers use position sensitive detectors that can detect electrons landing at different locations. By way of example, the detector may include a microchannel plate that can produce signals from detection of electrons at multiple locations in parallel and produce a separate signal for each location or "channel". Because the signal at each location depends on the energy of electrons that impinge on the detector at that an electron energy spectrum can be obtained in a relatively short period of time, e.g., on the order of about 1 or 2 seconds. This is sufficiently fast that an Auger spectrum could be obtained in a high vacuum environment (about $10^{-6}$ to $10^{-7}$ torr) before more than about 1 to 3 monolayers of adsorbates from background gas would build up on the sample.

The system 500 may also include a semiconductor tool such as an analysis tool 594, which may be, e.g., a metrology of review tool or an inspection tool, such as a reticle or mask inspection tool. The Analysis tool 594 may be equipped with the electron detection system 592, such as, e.g., an electron beam metrology of review tool equipped with an electron detection system having an S-curve analyzer. The S-curve analyzer may also use a position sensitive detector to produce a signal that corresponds to the secondary electron spectrum. By way of example, and not by way of limitation, the system 500 may include some or all of the features of methods and apparatus described in U.S. Pat. No. 7,635,842, the entire contents of which are incorporated by reference herein, such as, e.g., an electron detection system integrated into the vacuum chamber of a semiconductor tool as described in that disclosure. By way of further example, and not by way of limitation, the system 500 may include some or all of the features of methods and apparatus described in U.S. Pat. No. 8,421,030, the entire contents of which are incorporated by reference herein, such as, e.g., an S-curve electron energy analyzer as described in that document.

The system 500 may include a non-transitory computer readable medium configured to implement a method of Auger electron spectroscopy analysis in accordance with various aspects of the present disclosure. The non-transitory computer readable medium may further include one or more databases of one or more stored elemental spectral signatures.

Figure 6:
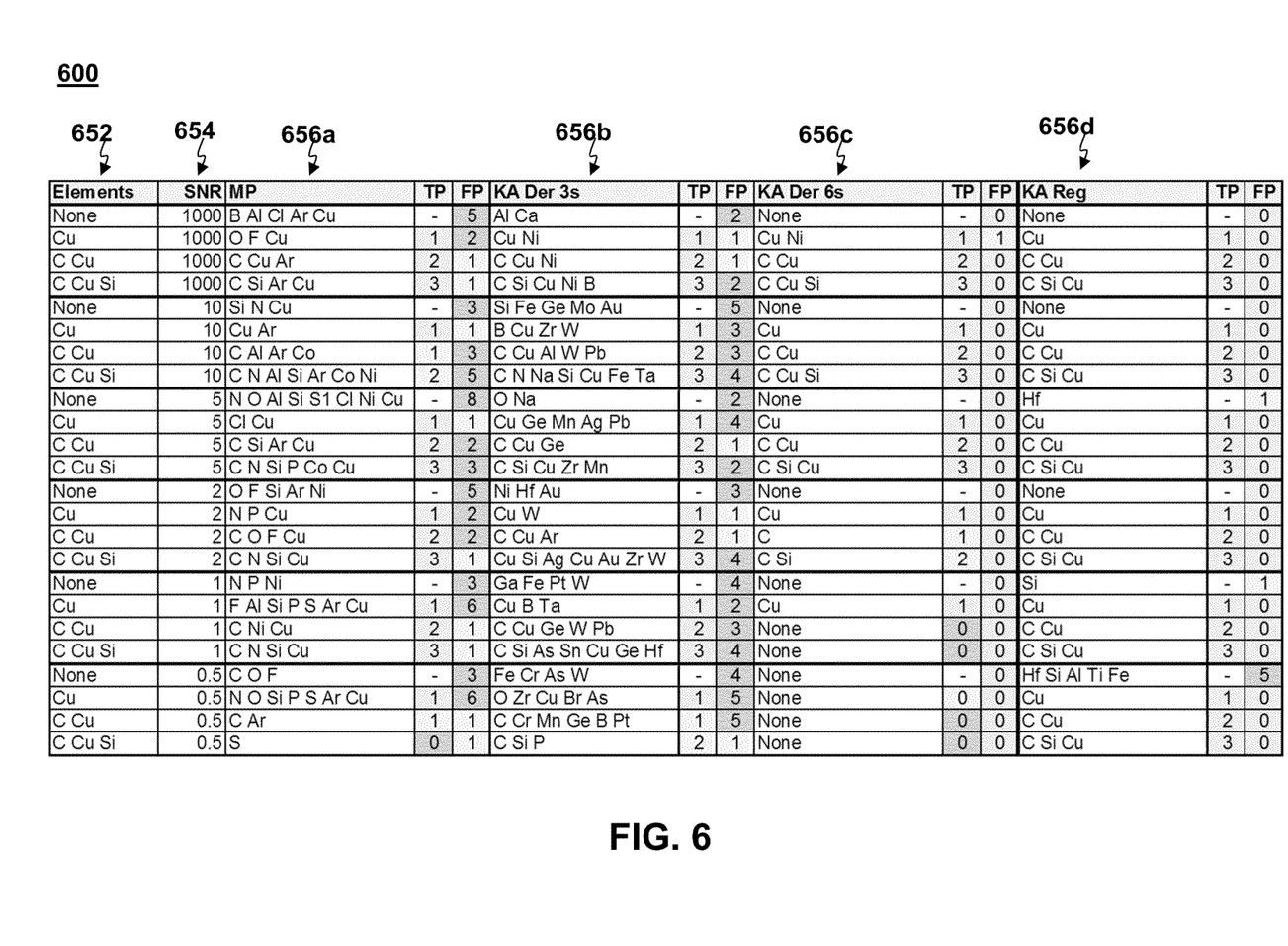
FIG. 6 is a table depicting performance results of various Auger elemental identification techniques.

FIG. 6 depicts performance results 600 of several Auger elemental identification techniques. In particular, performance results from three derivative based techniques 656a-c are depicted, as well as a regression based technique 656d performed in accordance with aspects of the present disclosure. The table depicts the elements present in a target sample from which the input spectrum under test is obtained in column 652, as well as a corresponding signal to noise ratio (SNR) of the input spectrum at 654. The elements positively identified by each method are depicted at 656a-d, as well as their corresponding true positive (TP) and false positive (FP) rates. The techniques MP at 656a, KA Der 3s at 656b, and KA Der 6s at 656c take the derivatives of the input signals in order to identify species based on peak locations corresponding to the Auger electrons in the signal. The technique KA Reg at 656d uses multilinear regression in accordance with aspects of the present disclosure in order to determine correlation between Auger spectra in the input signal with stored elemental spectral signatures. As can be seen from the table 600, the technique 656d provides significantly improved performance compared to the derivate based techniques 656a-c. In particular, a near perfect true positive identification rate of elements in the input spectrum for the entire range of input signals is achieved, not only for the relatively clear and high quality input signals at the top of the table, but also for the relatively noisy signals near the bottom.

CONCLUSION

Aspects of the present disclosure provide improved performance compared to traditional techniques for processing Auger spectral data. Using multilinear regression in accordance with aspects of the present disclosure can make use of broad stored elemental spectral signatures, as opposed to narrow peaks, thereby utilizing more information characteristic of elemental species to characterize species present in a target material. Additionally, the impact of resolution, shift, and noise of the input spectrum can be diminished, and the problem of peak ambiguity between different species can be automatically resolved. Moreover, the analytical techniques can be configured to directly output confidence and composition of the species present in the target material. A background signal unique to each input signal can be accurately estimated in accordance with techniques described herein, and multilinear regression can be performed on the normalized signal to provide accurate characterization of species present in the target material.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method of Auger spectral analysis of an input spectrum, the input spectrum including an Auger spectrum, the method comprising:
   conditioning the input spectrum to generate a normalized input spectrum;
   determining a statistical correlation between the normalized input spectrum and one or more stored elemental spectral signatures; and
   characterizing species in the input spectrum from the statistical correlation,
   wherein said conditioning the input spectrum includes estimating a background signal of non-Auger electrons in the input spectrum and subtracting the estimated background signal from the input spectrum.

2. The method of claim 1, wherein the estimated background signal is a convex envelope of the input spectrum and said estimating the background signal include using a convex hull algorithm to calculate the convex envelope.

3. The method of claim 1, wherein said determining statistical correlation includes performing multilinear regression on the normalized input spectrum against the stored elemental spectral signatures.

4. The method of claim 1, wherein said conditioning the input spectrum further includes filtering the input spectrum to remove noise from the input spectrum.

5. The method of claim 4, wherein said filtering the input spectrum includes applying a Savitzky-Golay smoothing filter to the input spectrum.

6. The method of claim 4, wherein said filtering the input spectrum includes applying a Gaussian filter to the input spectrum.

7. The method of claim 4, wherein said filtering the input spectrum includes applying a binomial filter to the input spectrum.

8. The method of claim 4, wherein said filtering the input spectrum includes applying a boxcar filter to the input spectrum.

9. The method of claim 1, further comprising acquiring the input spectrum, wherein said acquiring the input spectrum includes directing a beam of electrons at a target and determining an energy spectrum of secondary electrons emitted from the target with an Auger detection system.

10. The method of claim 9, wherein the target is a defect on a semiconductor wafer.

11. The method of claim 9, wherein the Auger detection system is equipped in a Metrology of review tool.

12. The method of claim 1, wherein said conditioning the input spectrum further includes subtracting a reference spectrum from the input spectrum.

13. The method of claim 12, further comprising:
acquiring the input spectrum, wherein acquiring the input spectrum includes directing a beam of electrons at a defect on a semiconductor wafer and determining an energy spectrum of secondary electrons emitted from the defect with an Auger detection system; and
acquiring the reference spectrum, wherein said acquiring the reference spectrum includes directing a beam of electrons at target on the semiconductor wafer that does not have the defect and determining an energy spectrum of secondary electrons emitted from the target with the Auger detection system.

14. The method of claim 1, wherein said characterizing species includes identifying elements in the input spectrum.

15. The method of claim 14, wherein said characterizing species further includes determining concentrations of the identified elements.

16. The method of claim 14, wherein said characterizing species further includes determining confidence levels of the identified elements.

17. A system comprising:
a processor unit;
a memory unit coupled to the processor unit;
a plurality of elemental spectral signatures embodied in the memory unit; and
program instructions embodied in the memory unit an executable by the processor unit, wherein execution of the program instructions by the processor unit causes the processor unit to implement a method of Auger spectral analysis of an input spectrum, the input spectrum including an Auger spectrum, the method comprising:
conditioning the input spectrum to generate a normalized input spectrum;
determining statistical correlation between the normalized input spectrum and the elemental spectral signatures; and
characterizing species in the input spectrum from the statistical correlation,
wherein said conditioning the input spectrum includes estimating a background signal of non-Auger electrons in the input spectrum and subtracting the estimated background signal from the input spectrum.

18. The system of claim 17, further comprising an Auger detection system, wherein the method further comprises acquiring the input spectrum, wherein said acquiring the input spectrum includes directing a beam of electrons at a target and determining an energy spectrum of secondary electrons emitted from the target with the Auger detection system.

19. The system of claim 18, wherein the Auger detection system is equipped in a Metrology of review tool.

20. A non-transitory computer readable medium having a plurality of elemental spectral signatures and program instructions embodied therein, wherein execution of the program instructions by a processor unit causes the processor unit to perform a method of Auger spectral analysis of an input spectrum, the input spectrum including an Auger spectrum, the method comprising:
conditioning the input spectrum to generate a normalized input spectrum;
determining statistical correlation between the normalized input spectrum and the stored elemental spectral signatures; and
characterizing species in the input spectrum from the statistical correlation,
wherein said conditioning the input spectrum includes estimating a background signal of non-Auger electrons in the input spectrum and subtracting the estimated background signal from the input spectrum.

* * * * *